United States Patent [19]

Heidgen

[11] Patent Number: Plant 6,354

[45] Date of Patent: Oct. 25, 1988

[54] GERANIUM NAMED PEACH DELIGHT

[76] Inventor: Charles F. Heidgen, 821 Walnut St., Batavia, Ill. 60510

[21] Appl. No.: 782,735

[22] Filed: Oct. 1, 1985

[51] Int. Cl.[4] ..... H01H 5/00

[52] U.S. Cl. ..... Plt./68

[58] Field of Search ..... Plt./68

*Primary Examiner*—Robert E. Bagwill

[57] ABSTRACT

A new and distinct variety of geranium plant, Peach Delight, characterized by its cascading growth habit; its large, peach-colored, double blossoms; its continuous blooming habit; its lightly zoned, large, medium-green foliage; and its heat tolerance.

1 Drawing Sheet

The present discovery, hereinafter referred to by the cultivar name, Peach Delight, relates to a new and distinct geranium plant.

BACKGROUND

Peach Delight is a new and improved variety which has resulted from definite breeding programs and experiments carried on by me in my greenhouses at 821 Walnut St., Batavia, Ill. Our experiments commenced in March, 1977 and are being carried on continuously. This seedling, 79×015A, resulted from a cross between Deacon Coral Reef, an unpatented, floribunda, zonal geranium and Orangesonne, an unpatented zonal geranium.

Asexual reproduction of Peach Delight has been accomplished from vegetative cuttings in my greenhouses in Batavia, Ill. Examination of plants so propagated has demonstrated that the combination of characteristics herein disclosed for Peach Delight are firmly fixed and retained through successive generations of asexual reproduction.

SUMMARY

The new and patentable characteristics of Peach Delight reside in its cascading growth habit, its large-sized medium green leaves with very light zonation, its continuous blooming habit, its distinctive peach-colored, double flower and its heat tolerance.

DESCRIPTION OF DRAWING

The photograph shows the plant and flower of a fully developed geranium of the new variety, Peach Delight.

BOTANIC DESCRIPTION

The Plant

Growth: Peach Delight is a continuous bloomer with a distinctive peach-colored, double blossom. The flower head (truss) is of a large size and very resistant to shattering. It has a slightly upright, but procumbent growth habit which gives a cascading effect. Growth rate is rapid, producing a typical 10" flowering basket in 10–12 weeks from four 2¼ inch plants using standard commercial culture. Peach Delight is also Ethrel responsive.

Blooming habit: A continuous bloomer, throughout the year, outdoors or in the greenhouse. A mature 10" basket would typically produce 13–21 heads at one time. This plant is heat tolerant and blooms well all through the summer, but might bloom somewhat less in the shorter, darker days of winter.

Inflorescence: Large-sized head, rounded as it opens, measuring 3½–4¼ inches in diameter.

Foliage:

*Quantity.*—Abundant.

*Size.*—Large, 2½–3½ inches across.

*Color.*—Scheeles Green)(860) with Parsley Green(00962/3) zone. (The Royal Horticultural Society Horticultural Colour Chart)

*Texture.*—A pubescent upper and lower surface.

Stem: Thick, normal internodes, quite free branching, procumbent growth habit.

Petiole: Long, 2–3½ inches long, same color as leaf.

THE FLOWER

Truss:

*Size.*—Large, 3½–4¼ inches in diameter.

*Shape.*—Rounded, a globe as it opens.

*Number of florets.*—Variable, range from 23–55, average 35–45.

*Lasting quality.*—Average. Blooms remain 5–11 days, longer if cool and dry.

Bud:

Sepals.—Short, somewhat pointed.

*Color.*—Orient Pink(416) (The Royal Horticultural Society Horticultural Colour Chart).

*Form.*—Rounded, almost pointed.

Florets:

*Size.*—1–1½ inches across.

*Petalage.*—Double, 9–11 petals.

*Color.*—Azalea Pink(618/1) (The Royal Horticultural Society Horticultural Colour Chart).

Texture: Soft and glowing.

Form: Double flower, petals range from ⅓ to ¾ inch wide.

Lasting quality: Average floret lasts from 4–8 days. The truss lasts up to 10–13 days.

Behavior: When the plant begins to flower, its blooming habit makes a very striking display of beautiful peach-colored blossoms against the large, lightly zoned, medium-green foliage.

Having thus disclosed my invention, I claim:

1. A new and distinct variety of geranium plant, substantially as shown and described, characterized by its cascading growth habit; its large, peach-colored, double blossoms; its continuous blooming habit; its lightly zoned, large, medium-green foliage; and its heat tolerance.

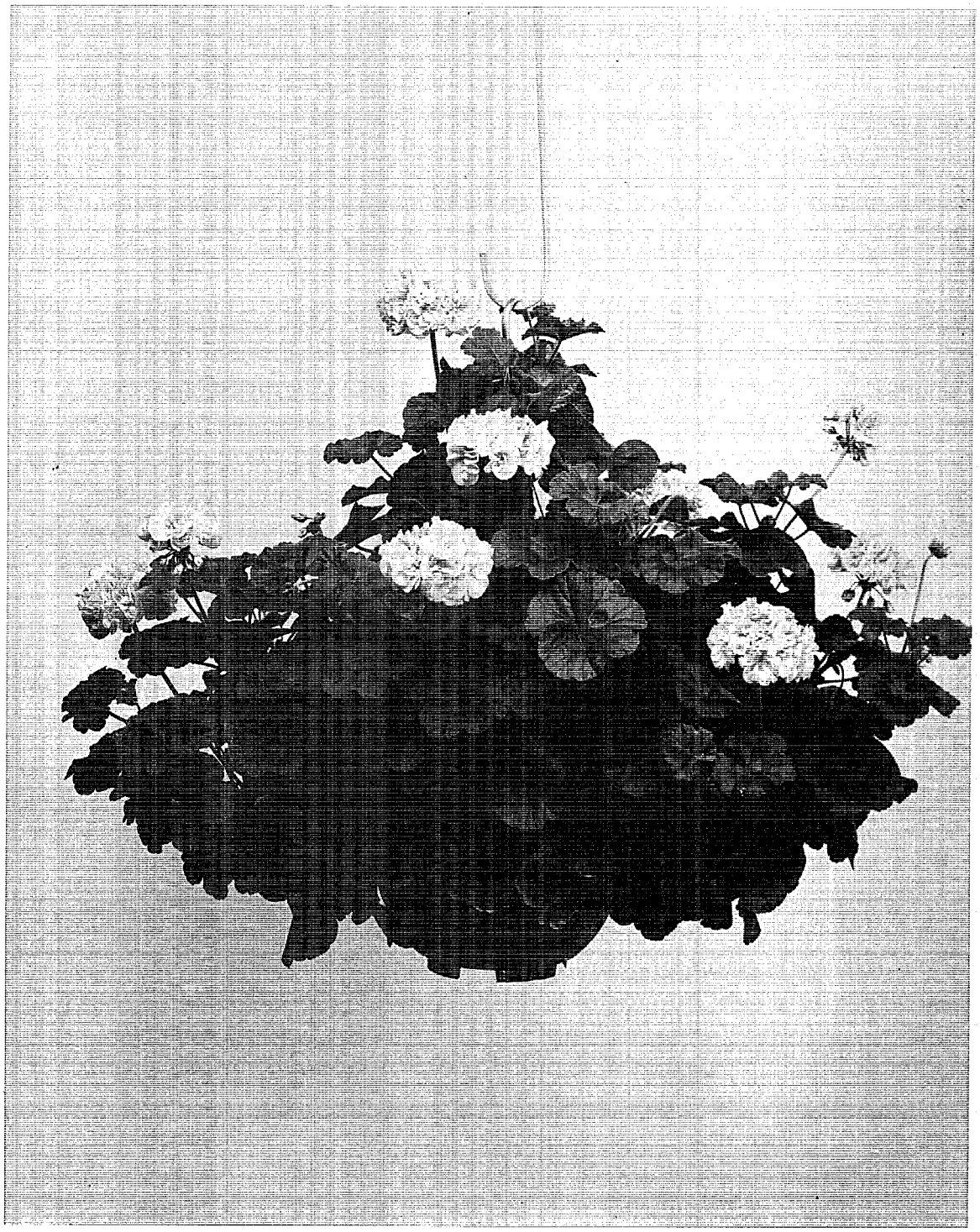

* * * * *